(12) United States Patent
Lucon et al.

(10) Patent No.: US 9,964,503 B2
(45) Date of Patent: May 8, 2018

(54) METHODS AND SYSTEMS FOR DETECTING FLAWS IN AN OBJECT

(71) Applicant: Resodyn Corporation, Butte, MT (US)

(72) Inventors: Peter A. Lucon, Buttle, MT (US); Lawrence C. Farrar, Butte, MT (US)

(73) Assignee: Resodyn Corporation, Butte, MT (US)

( * ) Notice: Subject to any disclaimer, the term of this patent is extended or adjusted under 35 U.S.C. 154(b) by 316 days.

(21) Appl. No.: 14/434,039

(22) PCT Filed: Oct. 21, 2013

(86) PCT No.: PCT/US2013/065917
§ 371 (c)(1),
(2) Date: Apr. 7, 2015

(87) PCT Pub. No.: WO2014/063148
PCT Pub. Date: Apr. 24, 2014

(65) Prior Publication Data
US 2015/0253266 A1  Sep. 10, 2015

Related U.S. Application Data

(60) Provisional application No. 61/795,567, filed on Oct. 19, 2012.

(51) Int. Cl.
*G01N 25/72* (2006.01)
*G01N 29/06* (2006.01)
(Continued)

(52) U.S. Cl.
CPC ............... *G01N 25/72* (2013.01); *G01J 5/02* (2013.01); *G01N 29/069* (2013.01);
(Continued)

(58) Field of Classification Search
CPC ................................................... G01N 25/72
(Continued)

(56) References Cited

U.S. PATENT DOCUMENTS 4,480,480 A * 11/1984 Scott ................... E02B 17/0034
702/41
5,410,406 A * 4/1995 Webster ................. G01B 9/021
356/35.5
(Continued)

FOREIGN PATENT DOCUMENTS

DE   1020070 43 364 A1   4/2009

OTHER PUBLICATIONS

Kang ("Excitation Method for Thermosonic Non-destructive Testing" (2008). Imperial College London Mechanical Engineering PhD theses, https://spiral.imperial.ac.uk/handle/10044/1/1411).*
(Continued)

*Primary Examiner* — Clayton E Laballe
*Assistant Examiner* — Leon W Rhodes, Jr.
(74) *Attorney, Agent, or Firm* — McDermott Will & Emery LLP

(57) ABSTRACT

The present application is directed towards systems and methods for evaluating the integrity of objects through non-destructive means. The objects are evaluated for flaws and defects through the use of applied acoustic energy. The applied acoustic energy creates a dynamic response of the object being evaluated to determine the location of any flaws or defects in the object. During excitation, the flaws and defects in a sample object generate heat at the damaged or defective regions through frictional interactions of the discontinuities. A flaw detection system includes, a plurality of acoustic energy sources to excite an object, a camera to record metrics of the response of the object and a processor configured to receive and analyze the response of the object.

20 Claims, 11 Drawing Sheets

(51) Int. Cl.
*G01J 5/02* (2006.01)
*G01J 5/00* (2006.01)

(52) U.S. Cl.
CPC ............... *G01J 2005/0081* (2013.01); *G01N 2291/0231* (2013.01); *G01N 2291/0289* (2013.01)

(58) Field of Classification Search
USPC .......................................................... 374/5
See application file for complete search history.

(56) References Cited

U.S. PATENT DOCUMENTS

| | | | | |
|---|---|---|---|---|
| 6,786,098 B2* | 9/2004 | Bates | ............... | G01N 25/72 250/334 |
| 7,119,338 B2* | 10/2006 | Thompson | ............. | G01N 25/72 250/341.6 |
| 7,122,801 B2* | 10/2006 | Favro | ............... | G01N 3/60 250/330 |
| 8,220,991 B2* | 7/2012 | Safai | ............... | G01N 25/72 156/272.2 |
| 9,410,853 B2* | 8/2016 | Zombo | ............... | G01N 25/72 |
| 2002/0121602 A1 | 9/2002 | Thomas et al. | | |
| 2004/0089811 A1 | 5/2004 | Lewis et al. | | |
| 2004/0159790 A1 | 8/2004 | Thompson et al. | | |
| 2004/0245469 A1 | 12/2004 | Favro et al. | | |
| 2007/0045544 A1 | 3/2007 | Favro et al. | | |

OTHER PUBLICATIONS

Zhang ("Frequency and load mode dependence of Vibrothermography" (2010). Iowa State University Graduate Theses and Dissertations. 11293, http://lib.dr.iastate.edu/etd/11293).*

Engholm ("A Narrowband Ultrasonic Spectroscopy Technique for the Inspection of Layered Structures", (2006), Uppsala University Licentiate thesis, pp. 21-24).*

International Preliminary Report on Patentability for International Application No. PCT/US2013/065917, dated Apr. 30, 2015.

International Search Report and Written Opinion of the International Searching Authority for International Application No. PCT/US2013/065917, dated Jan. 27, 2014.

* cited by examiner

Figure 3
300

302 — determining a location to place an acoustic energy source

304 — applying a static preload

306 — exciting the object at the determined locations

308 — creating a thermogram to identify flaws and characterize them if found

310 — determining a confidence factor

402 excite the object with a range of frequencies 404 determine the resonant response of the object to excitation 406 excite the object at a peak resonant frequency 408 analyze the modal response to identify anti-nodes

602 comparing a cold image to active images to create a thermogram 604 filtering the thermogram to remove noise 606 converting the thermogram image to a binary image 608 applying a density filter to the thermogram 610 analyze the thermogram to determine areas that generated heat

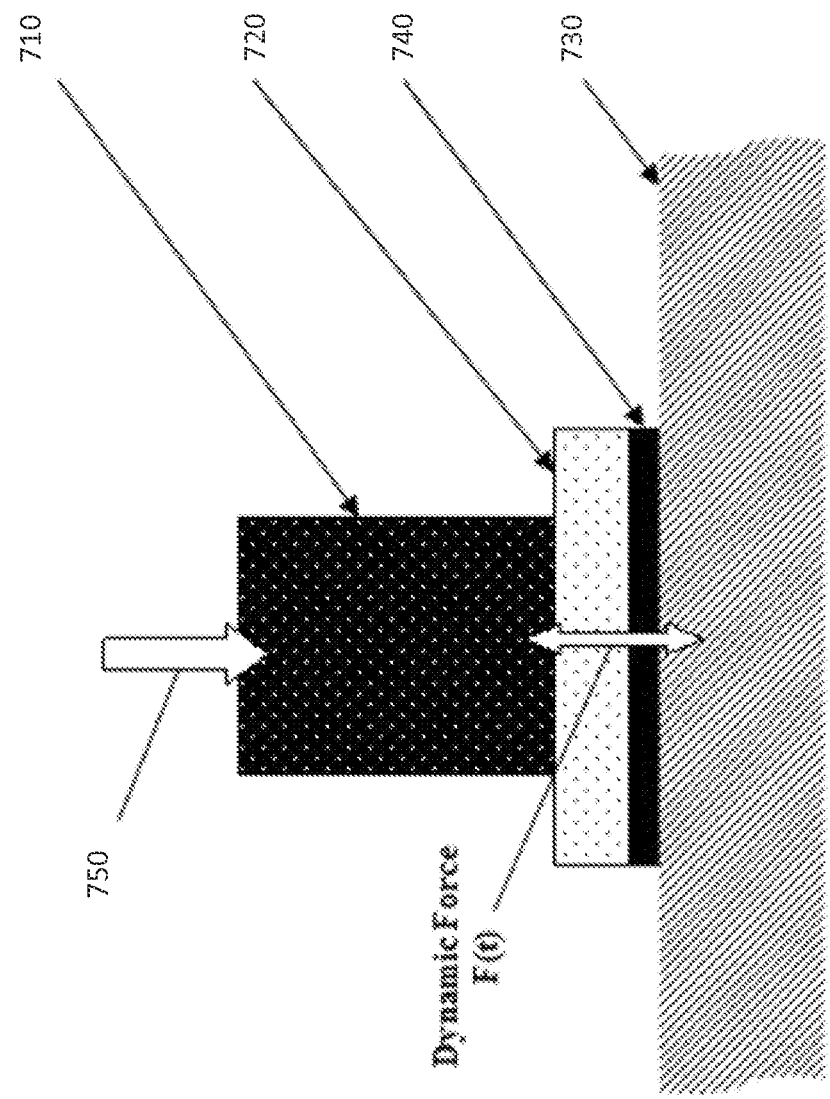

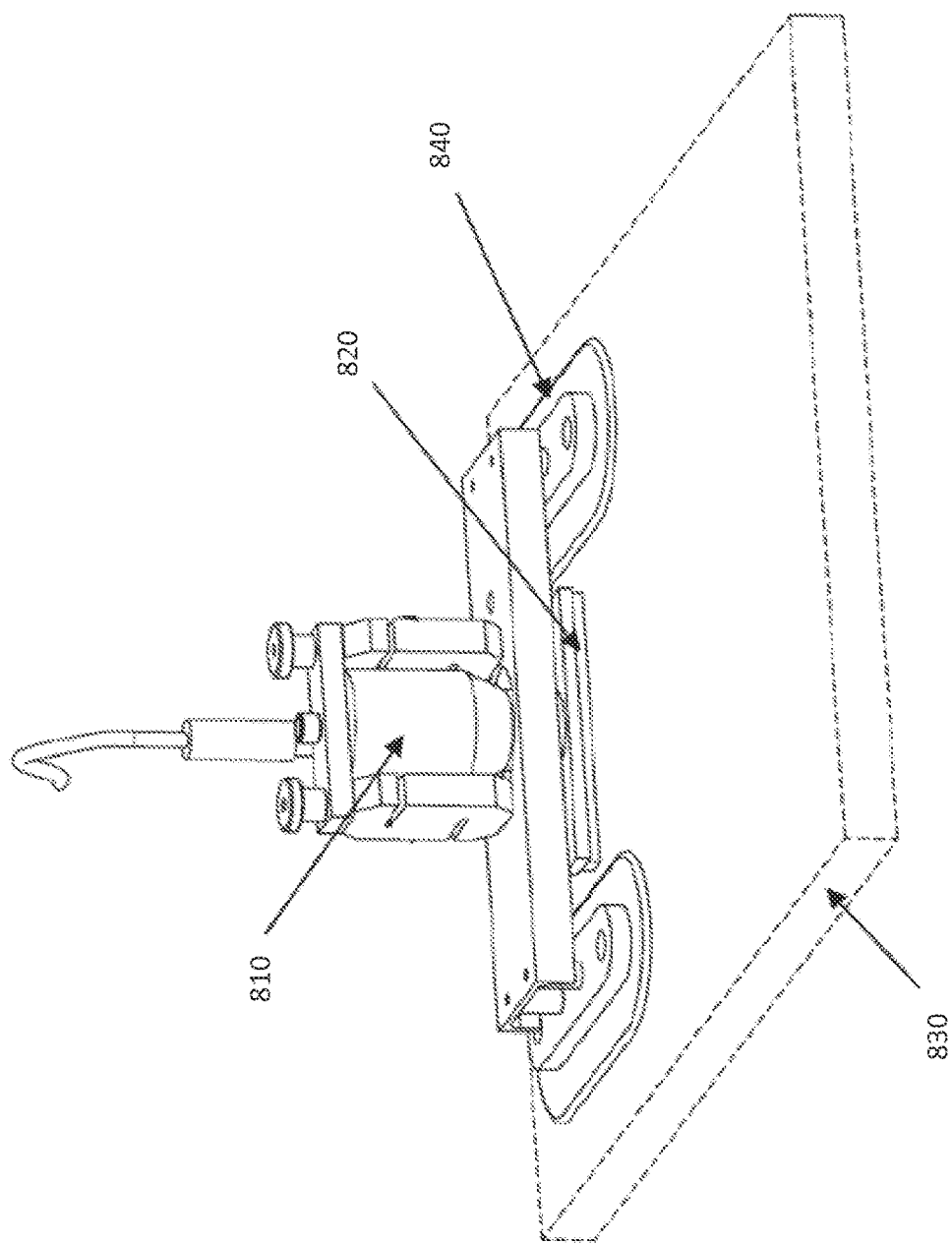

METHODS AND SYSTEMS FOR DETECTING FLAWS IN AN OBJECT

CROSS-REFERENCE TO RELATED APPLICATIONS

The present application is a U.S. National Stage under 35 U.S.C. § 371 of International Application No. PCT/US2013/065917, filed Oct. 21, 2013, entitled "Methods and Systems for Detecting Flaws in an Object", and claims the benefit of U.S. Provisional Patent Application No. 61/795,567, filed Oct. 19, 2012, entitled "Non-Destructive Device that Detects and Identifies Flaws and Tests Strength of Bonds." The entire contents of each of the above applications are incorporated herein by reference.

FIELD OF THE INVENTION

The present application is in the technical field of non-destructive testing and evaluation of objects.

BACKGROUND

Current methods and systems for identifying flaws and defects in an object do not allow for repeatable results and can result in damage to the object under test. Therefore, current methods and system for identifying flaws and defects in objects are not conducive to a maintenance program to monitor the integrity of objects over time.

SUMMARY

The present application is directed towards system and methods for non-destructive testing and evaluation of objects to determine the integrity of the object. The application of acoustic energy to excite objects provides a means to test and identify flaws and defects in the object without damaging the object. As a result, the process can be repeated, for example, as part of a routine maintenance program.

More particularly, such systems and methods involve an acoustic energy source applying acoustic energy to a sample object and the response of the object to the acoustic energy is analyzed to determine certain characteristics of the object and identify flaws and defects in the object. Flaw detections systems, as will be discussed in greater detail below, can include a camera and other sensing devices to record metrics of the response of the object and a processor configured to receive and analyze such metrics.

In one aspect, the present disclosure is related to a method for detecting flaws in an object. The method includes determining a location on the object to place an acoustic energy source, applying a static preload between a contact point of the acoustic energy source and the object, applying acoustic energy to excite the object, recording a thermal response of the object to the application of acoustic energy, and analyzing the thermal response to identify flaws within the object. The method further includes analyzing the resonant response of the object to identify anti-node locations. In some implementations, the method includes determining a sufficient number of locations such that substantially the entire surface of the object is excited to amplitudes that would generate enough heat to be detected by flaw detection systems, for example as or near anti-nodes. In other implementations, the method includes visually identifying anti-node locations of the object while exciting the object at one or more resonant frequencies of the object. When multiple resonant frequencies are applied, in some implementations they are applied serially, while in other implementations they are applied simultaneously. In some implementations, the acoustic energy source is placed in contact with the object via an energy transfer material. Further, the method includes the acoustic energy source is placed in contact with the object via an energy transfer material and a contact plate. In some implementations, the static preload is greater than the dynamic force induced in the object by the acoustic energy source. In some implementations, the method includes applying the acoustic energy at a frequency ranging from about 100 Hz to about 60 kHz. In some implementations, the acoustic energy is applied for a time ranging from about one second to about 10 minutes.

In some implementations, the thermal response is recorded by at least one of: an infrared camera and an embedded temperature sensor. In some implementations, The method includes comparing an image of the object taken prior to exciting the object to an image of the object taken while the object is being excited to determine a transient response of the object. Further, the method can include determining at least one of: a depth of a defect, a size of a defect, and a location of the defect. In some implementations, the object is a bond joint. Further, the method includes analyzing the bond joint to detect a disband or a delamination in the bond joint.

In another aspect, the present disclosure is related to a system for detecting flaws in an object. The system includes a plurality of acoustic energy sources, a temperature sensor and a processor communicatively coupled to the temperature sensor. The processor may be configured to receive data indicative of a thermal response of the object to the application of acoustic energy applied to the objet by the plurality of acoustic energy sources and to analyze the thermal response to identify and determine characteristics of flaws and defects in the object.

In the system, each of the acoustic energy sources may be one of: a piezoelectric transducer, a voice coil, or a rotating eccentric mass. In some implementations, the temperature sensor is an infrared camera. The system further can include a contact plate to transfer acoustic energy from at least one acoustic energy source to the object. The system can include an energy transfer material to facilitate transfer of acoustic energy from the contact plate to the surface of the object. In some implementations, the energy transfer material is duct tape. In some implementations, the system further includes at least one of: an accelerometer, a dynamic force gauge, a Doppler vibrometer. In some such implementations, the processor is configure to process the output of the accelerometer, dynamic force gauge, or Doppler vibrometer to determine placement locations on the object for the plurality of acoustic energy sources. In some implementations, the processor is configured to generate and analyze thermal difference thermograms based on temperature data received from the temperature sensor before and during excitation of the object by the plurality of acoustic energy sources to determine a transient thermal response of the object.

In another aspect, the present disclosure is related to a method for detecting flaws in a bond joint. The method includes determining a location on the bond joint to place an acoustic energy source, applying a static preload between a contact point of the acoustic energy source and the bond joint, applying acoustic energy to excite the bond joint, recording a thermal response of the bond joint to the application of acoustic energy, and analyzing the thermal response to identify flaws within the bond joint. In some implementations, the acoustic energy source is placed in contact with the bond joint via an energy transfer material. In other implementations, the acoustic energy source is placed in contact with the bond joint via an energy transfer material and a contact plate.

In some implementations, the static preload is generated by a vacuum source. Further, the static preload may be greater than the dynamic force induced in the bond joint by the acoustic energy source. The method further includes applying the acoustic energy comprises applying the acoustic energy at a frequency ranging from about 100 Hz to about 60 kHz. In some implementations, the acoustic energy is applied for a time ranging from about 1 second to about 10 minutes. Further, the method includes recording the thermal response by at least one of: an infrared camera and an embedded temperature sensor. The method includes comparing an image of the bond joint taken prior to exciting the bond joint to an image of the bond joint taken while the bond joint is being excited to determine a transient response of the object. In some implementations, analyzing the thermal response further includes determining at least one of: a depth of a defect, a size of a defect, and a location of the defect. Further, the method includes detecting by at least one accelerometer a shockwave resulting from a failure of the bond joint in response to the applied acoustic energy

BRIEF DESCRIPTION OF THE FIGURES

The foregoing and other objects, aspects, features, and advantages of the disclosure will become more apparent and better understood by referring to the following description taken in conjunction with the accompanying drawings, in which:

FIG. 3 is a flow diagram of an example method for detecting flaws in an object;

FIG. 4 is a flow diagram of an example method for determining placement for an acoustic energy source;

FIG. 8 is a flow diagram of an example method for analyzing response metrics;

FIG. 10 is a diagrammatic cross-sectional view of an example excitation portion of a flaw detection system; and FIG. 11 is a perspective view of another example excitation portion of a flaw detection system.

DETAILED DESCRIPTION OF THE INVENTION

Described herein are methods and systems for detecting flaws and defects in objects through non-destructive means. The various concepts introduced above and discussed in greater detail below may be implemented in any of numerous ways, as the described concepts are not limited to any particular manner of implementation. Examples of specific implementations and applications are provided primarily for illustrative purposes.

Using the systems and methods disclosed herein, test objects are evaluated for flaws and defects through the use of applied acoustic energy. The applied acoustic energy induces a dynamic thermal response in the object being evaluated, which can be analyzed to determine the location of any flaws or defects in the object. Flaws and defects can be in the form of cracks, disbands, delamination, or embedded foreign objects in the object.

During excitation, flaws and defects in the sample object generate heat at the damaged or defective regions through frictional interactions of discontinuities within the material that makes up the object. Accordingly, the application of acoustic energy to these areas generates a response in the form of localized heat generation which can be detected by various instruments, such as an infrared camera or embedded temperature sensors. The infrared camera can detect heat generation, both on the surface of the sample object, as well as thermal heat generation that is internal to the object. Metrics of the response of the object to excitation can be evaluated and analyzed to determine locations, depth, and size of flaws and defects in the object. Further, the metrics can be analyzed to determine one or more confidence factors associated with the flaw detection or flaw characterization, as described further below.

Figure 1:
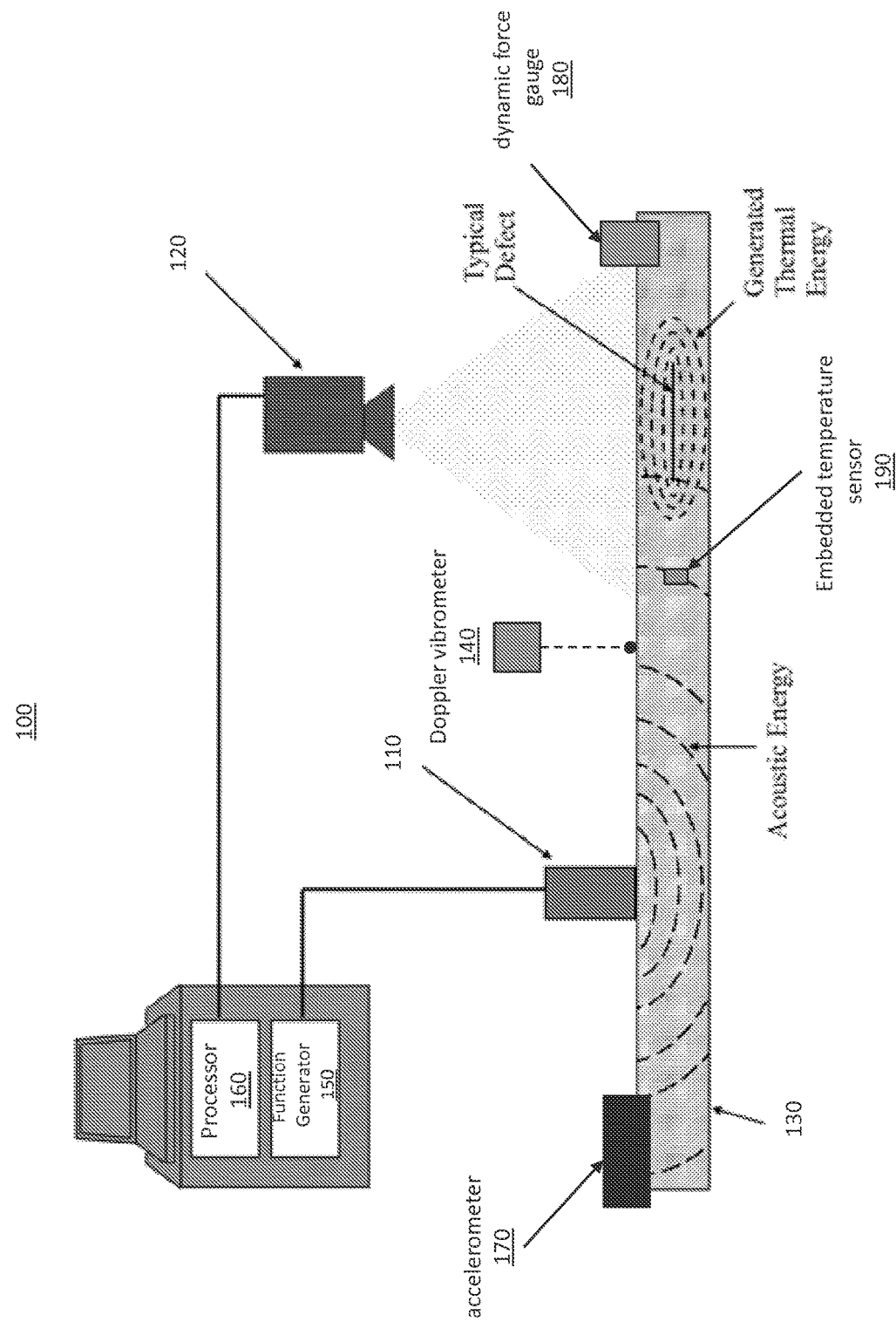
FIG. 1 is a diagrammatic view of one example implementation of a flaw detection system.

FIG. 1 is a diagrammatic view of one example implementation of a flaw detection system 100. The flaw detection system 100 includes an acoustic energy source 110, a camera 120, and a processor 160. As illustrated, the acoustic energy source can be placed in contact with an object 130 to detect flaws or defects in the object 130. To detect flaws in the object 130, the acoustic energy source 110 can be coupled to a function generator 150. The function generator 150 can generate different types of electrical waveforms over a wide range of frequencies to drive the acoustic energy source. In some implementations, the function generator 150 is one component of the processor 160.

Figure 2:
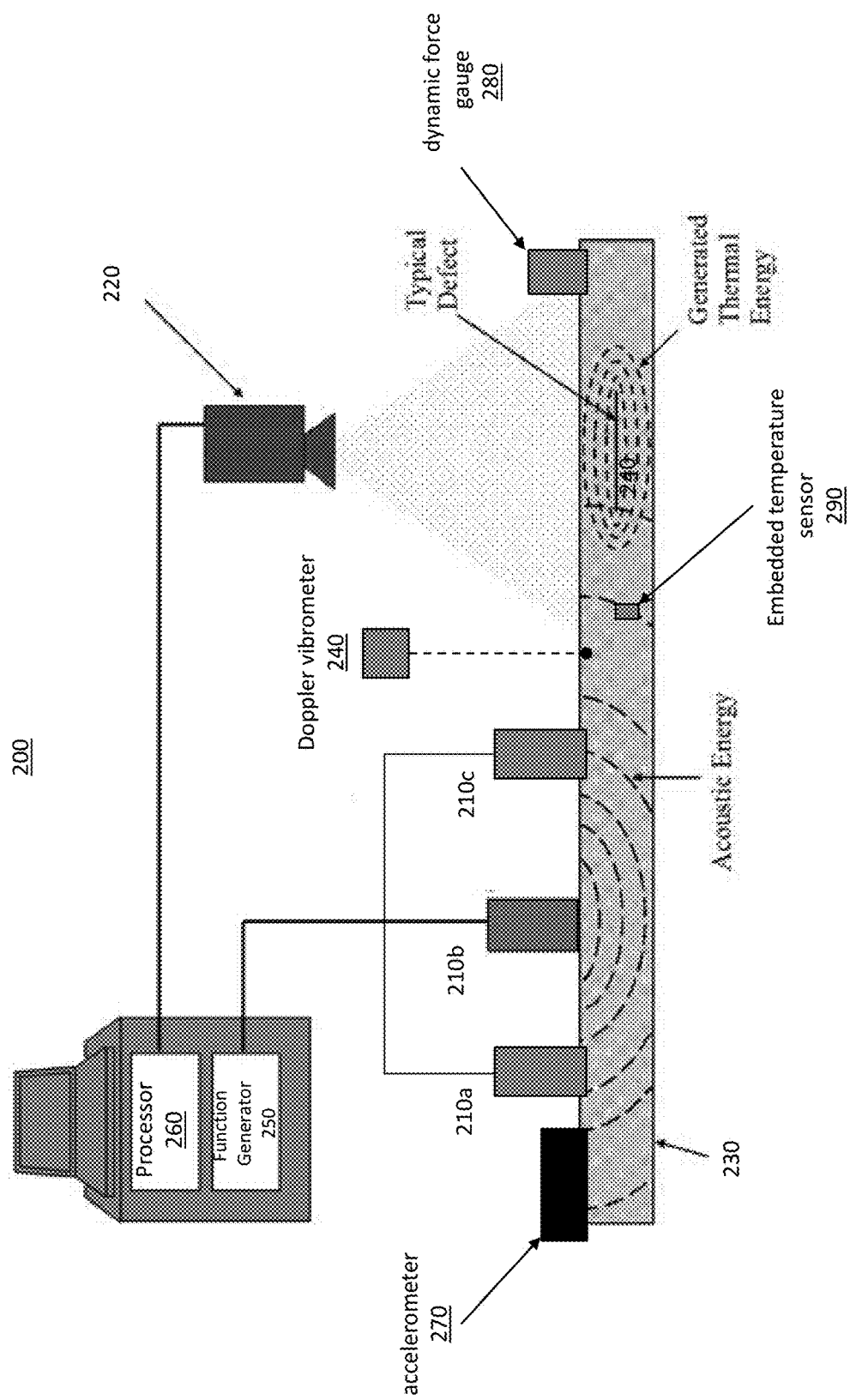
FIG. 2 is a diagrammatic view of another example implementation of a flaw detection system.

The acoustic energy source 110 can be any device that creates an output of a periodic load to the surface of an object 130, for example and without limitation, a piezoelectric transducer, a voice coil, or a rotating eccentric mass. In some implementations (for example, as shown in FIG. 2), the flaw detection system 100 includes a plurality of acoustic energy sources 110. In other implementations, the flaw detection system 100 includes one acoustic energy source 110.

The response of the object to the application of acoustic energy from the acoustic energy source 110 can be detected by several devices, for example the camera 120, an accelerometer 170, a dynamic force gauge 180, a Doppler vibrometer 140, and/or an embedded temperature sensor 190. In regards to the camera 120, the camera 120 can be any image capture device configured for monitoring and detecting heat patterns and/or localized heat generations of an object, such as an infrared camera.

The accelerometer 170 can be any device for measuring acceleration of an object subject to or involved in vibration (i.e., excitation). For example, the accelerometer 170 can measure the acceleration of the surface of the object 130 when it is excited by the acoustic energy source 110.

The dynamic force gauge 180 can be any device for measuring force during a testing of an object. In some implementations, the dynamic force gauge 180 can measure the force transmitted to the object 130 by the acoustic energy source 110. The use of the force gauge can be particularly beneficial in systems that include multiple acoustic energy sources. In such systems, the harmonic excitation resulting from the simultaneous application of acoustic energy from multiple transducers should be applied in a phase-synchronous fashion. The dynamic force gauge 180 can measure the force being applied at each acoustic energy source to ensure it is applied in a phase-synchronous fashion, as will be described later. The dynamic force gauge 180 can be mechanical or digital.

The Doppler vibrometer 140 can measure the response (i.e., the motion) of the object 130 to excitation by scanning a laser across the surface of the object 130. The Doppler vibrometer output can be analyzed to determine both the magnitude and the frequency of motion of multiple portions of the object. In some implementations, the output from the Doppler vibrometer 140 is an analog signal.

In some implementations, instead of or in addition to the camera 120, the flaw detection system 100 includes temperature sensors 190 embedded within the object under test. The embedded temperature sensors 190 can be any device that measures and collects metrics related to the temperature of the object 130. The embedded temperature sensor 190 can be embedded into a specific region of the object 130. In some implementations, multiple embedded temperature sensors 190 can be embedded into the object 130 to effectively monitor heat generation across the entire object.

The processor 160 includes a memory for storing and recording the metrics received from various devices of the flaw detection system 100. Further, the processor 160 includes several modules for handling the data associated with detecting flaws in the object 130. For example, the processor 160 includes a signal analysis module for analyzing signals representing the response of the object 130 to excitation, a response analysis module for processing collected metrics to determine a transient response of the object 130, and a confidence factor calculation module for calculating a confidence factor of detection of flaws and defects in the object 130.

In some embodiments, the processor 160 is a general purpose processor. A general purpose processor may be a microprocessor, or, any conventional processor, controller, microcontroller, or state machine. The processor 160 also may be implemented as a combination of computing devices, for example, a combination of a digital signal processor (DSP) and a microprocessor, a plurality of microprocessors, one or more microprocessors in conjunction with a DSP core, or any other such configuration. In some implementations, the aforementioned modules may be implemented by special purpose circuitry, e.g., ASICs or FPGAs, that is designed specifically for their particular functions. In some implementations, the modules are implemented as processor-executable software modules which may reside on a computer-readable medium. In some other implementations, the modules are implemented in a combination of hardware and software. Whether any particular functionality is implemented in hardware or software depends upon the particular application and design constraints imposed on the overall system.

FIG. 2 is a diagrammatic view of another example implementation of a flaw detection system 200. The flaw detection system 200 is similar to the flaw detection system 100, but instead of only one acoustic energy source, the flaw detection system 200 includes multiple acoustic energy sources 210a-210c. The flaw detection system further includes a camera 220, a processor 560 and a function generator 250. The plurality of acoustic energy sources 210 apply acoustic energy to the object 230 at various locations. In some cases, the object 230 includes multiple flaws and defects at various locations, including on the surface of the object 230 and/or internal to the object 230. To detect all of the flaws, multiple acoustic energy sources 210 apply acoustic energy to the surface of the object 230 to excite different locations. In some implementations, all of the acoustic energy sources 210 interacting with one object apply acoustic energy to the object 230 at the same frequency. In other implementations, the acoustic energy sources 210 apply acoustic energy at different frequencies at different locations.

Figure 5:
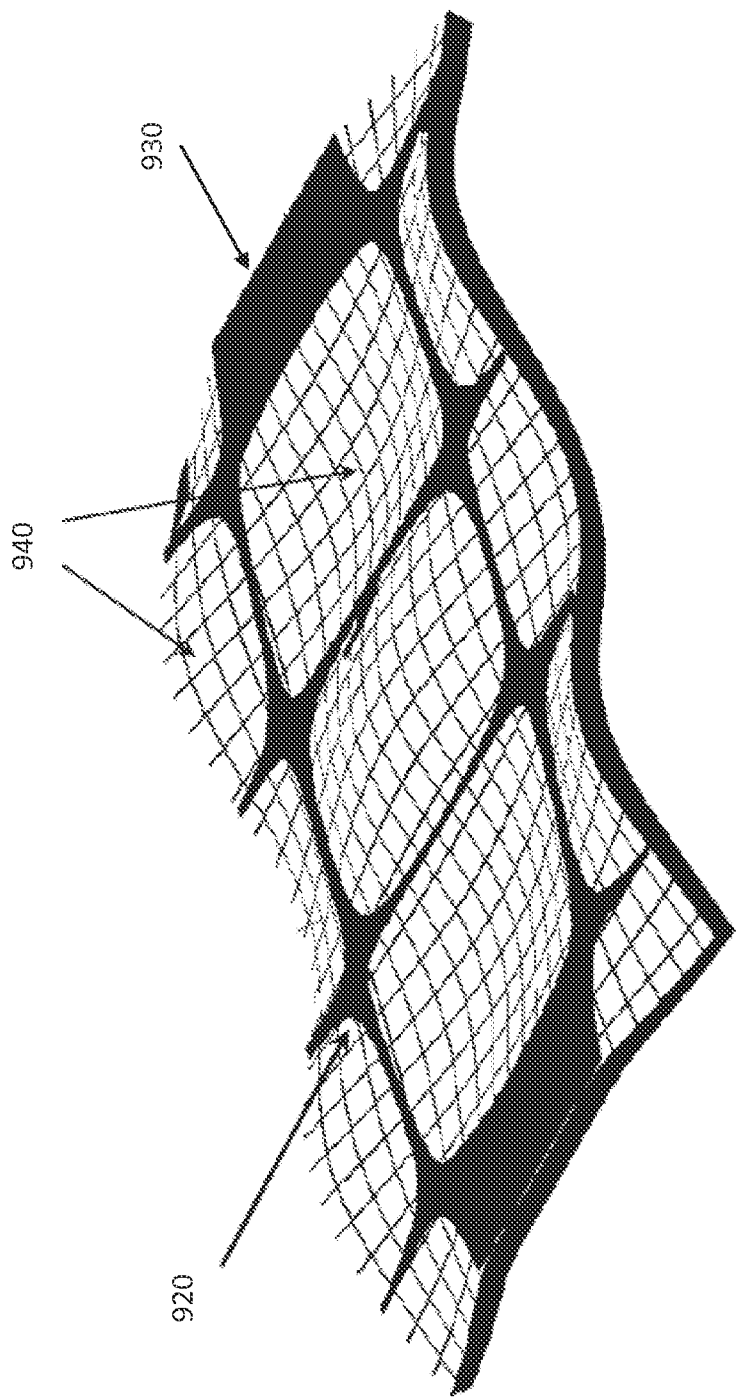
FIG. 5 is a perspective view of the modal response of an example excited object.

Ideally, the object is excited with enough acoustic energy sources 210 at enough locations at enough frequencies (in parallel, in series, or some in parallel and some in series), such that the entire object 230 under test is at some point during the test excited at or in close proximity to a resonant anti-node of the object (described further in relation to FIG. 5). In general, the object is excited such that a sufficient amount of the surface of the object 230 is excited to have a sufficient displacement magnitude that if a flaw were present in the object, the movement of the location with the flaw would generate enough heat to be detected (as described further below). The flaw detection system 200, which includes multiple acoustic energy sources 210, can accomplish this much faster than systems employing only a single acoustic energy source. By using multiple acoustic energy sources 210, the complete analysis of the object 230 being excited with all appropriate resonant frequencies, in some cases, can be accomplished in one test.

To control the operating frequency of the multiple acoustic energy sources 210, the function generator 250 can be used. The function generator operates similar to the function generator 150 in FIG. 1, and can be coupled to each of the acoustic energy sources 210 to drive them at their respective frequencies. A range of frequencies under certain time constraints, similar to those ranges and time periods described above in regards to FIG. 1, can be used to excite the object 230.

As described in relation to the system 100, the response of the object 230 to the application of acoustic energy from the multiple acoustic energy sources 210 can be detected by several devices. For example, the response can be detected by the camera 220, an accelerometer 270, a dynamic force gauge 280, a Doppler vibrometer 240, and/or an embedded temperature sensor 290. The camera 220, the accelerometer 270, the dynamic force gauge 280, the Doppler vibrometer 240, and/or the embedded temperature sensor 290 can all be communicatively coupled to the processor 260 to transmit the collected metrics and data, detailing the response of the object 230.

The processor 260 is similar to the processor 260 described in regards to FIG. 1 and includes similar modules for receiving and analyzing data related to the response of the object 230 to excitation. For example, processor 260 includes a signal analysis module, a response analysis module, and a confidence factor calculation module.

FIG. 3 is a flow diagram of an example method 300 for detecting flaws in an object. The method 300 can be carried out using a flaw detection system, such as the flaw detection systems 100 and 200 of FIGS. 1 and 2. In a brief overview, the method 300 includes determining a location to place an acoustic energy source (Step 302), applying a static preload to couple the acoustic energy source to the object (Step 304), exciting the object at the placement locations (Step 306), creating a thermogram to identify flaws and characterize the flaws if found (Step 308), and determining a confidence factor (Step 310).

The method 300 includes determining a location on the object to place an acoustic energy source (Step 302). In some implementations, a location of where to place the acoustic energy source 110 on the object 130 is randomly selected.

However, random placement may result in sub par system performance. In general, it is desirable to place the acoustic energy sources on regions of the test object that experience high levels of displacement when excited by the frequency of acoustic energy applied by the acoustic energy source, for example at or near resonant anti-nodes. Such regions are referred to as anti-nodes, and are described further below in relation to FIG. 5. Driving the object at such locations results in increased object excitement, and greater heat generation at the location of defects, making such defects easier to detect.

In some implementations, instead of conducting a complete test using only random acoustic energy source placement locations, as illustrated in FIG. 4, desirable acoustic energy source placement locations on an object can be determined empirically by determining the resonant response of the object under test. Specifically, the resonant response is used to identify frequency-dependent anti-nodes on the object (described further below). In general, a sufficient number of excitation locations and corresponding frequencies are selected such that substantially the entire surface of the object under test is excited at a resonant anti-node (or sufficiently close thereto) at some point during the test procedure. The resonant anti-nodes can have various resonant mode shapes at different frequencies identified during the course of multiple tests.

FIG. 4 is a flow diagram of an example method 400 for determining placement for identifying anti-nodes of an object under test. The method 400 includes exciting the object with a range of frequencies (Step 402), determining a resonant response of the object to excitation (Step 404), exciting the object at the identified peak resonant frequencies (Step 406), and analyzing the modal response to the resonant excitation to identify resonant anti-nodes (Step 408).

To model the object, an acoustic energy source 110 can be used to excite the object 130 to at a range of frequencies (Step 402). The goal of this stage of the process is to identify resonant frequencies of the object under test. The frequency of the applied acoustic energy ranges from about 100 Hz to about 60 kHz. The energy can be applied at one or more locations selected initially at random or based on known characteristics of the object under test. The acoustic energy can be applied for a predetermined time. In some implementations, the acoustic energy is applied to the surface of the object 130 for about 90 seconds. In other implementations, the acoustic energy is applied to the surface of the object 130 for a few seconds up to about 10 minutes or any amount there between. To obtain data for a wide range of frequencies, the acoustic energy may be applied in the form of a frequency chirp or white-noise excitation.

Then, the method 400 includes determining a resonant response of object 130 to excitation (Step 404). When the object 130 is subjected to excitation, the response can be measured with devices such as the accelerometer 170 and the dynamic force gauge 180. For example, the accelerometer 170 can measure the acceleration of the surface of the object 130 when it is excited by the acoustic energy source 110. The dynamic force gauge 180 can measure the force applied to the object 130 by the acoustic energy source 110. When the object 130 is subject to periodic driving forces, these forces can produce large amplitude oscillations. The accelerometer 170 and the dynamic force gauge 180 can measure the driving point response of the object 130. Additionally, the accelerometer 170 and the dynamic force gauge 180 can be configured to transmit the collected metrics to the processor 160.

The signal analysis module of the processor 160 can receive these signals and determine the resonant response of the object 130. The frequencies at which the response amplitude is a relative maximum can be referred to as the system's resonant frequencies. In general, these frequencies, even at small periodic driving forces, can produce large amplitude oscillations. To identify the resonant frequencies, the signals collected detailing the response of the object 130 can then be transformed from the time domain to the frequency domain using a Fast Fourier Transform (FFT). Peaks identified in the FFT correspond to peak resonant frequencies of the object 130.

The peak resonant frequencies can then be used to excite the object 130 (Step 406). Multiple acoustic energy sources 110, as illustrated in FIG. 2, can be used to simultaneously excite different regions of the object 130 with different resonant frequencies. While the object 130 is excited at the appropriate frequencies, the Doppler vibrometer 140 can scan the surface of the object 130 to measure the resulting vibrations, which indicate the modal response of the object 130. The Doppler vibrometer 140 can measure the response (i.e., the motion) of the object 130 to excitation by scanning a laser across the surface of the object 130 and measuring the frequency and/or phase changes of the reflected laser light. The measurements recorded by the Doppler vibrometer 140 include a vibration amplitude and a frequency of the surface of the object 130. In some implementations, the Doppler vibrometer 140 can target specific areas on the surface of the object 130 that may be difficult to measure with other devices. The response metrics collected by the Doppler vibrometer 140 can be used to be compared against and verify the response metrics obtained by other devices, such as the accelerometer. The Doppler vibrometer 140 can be configured to transmit the response metrics to the processor 160. The signal analysis module of the processor 160 can analyze the modal response of the object 130 to the excitation.

By analyzing the modal response (mode shape) of the object 130 to excitation, areas of high acceleration and displacement can be identified (Step 408). The tests are repeated at each of the resonant frequencies until the entire (or substantially the entire) inspected area is subjected to an antinode response with sufficient displacement and high enough frequency. FIG. 5 is a perspective view of the modal response of an example excited object 900. FIG. 5 shows nodes 920 and anti-nodes 940 of the object 900 during excitation. Nodes 920 refer to low displacement regions in a vibrating, excited object. Anti-node 940 locations refer to high displacement regions in a vibrating, excited object. As illustrated in FIG. 5, the locations of the anti-nodes 940 are represented by peaks in the black and white grid sections of the object 930 and the locations of the nodes 920 are represented by the solid black regions of the object 930. As shown in FIG. 5, if more than one adjacent anti-node region is excited, the phase of the neighboring anti-node regions are typically 180° out of phase. Additionally, different anti-nodes 940 can have different displacement amplitudes.

Figure 6:
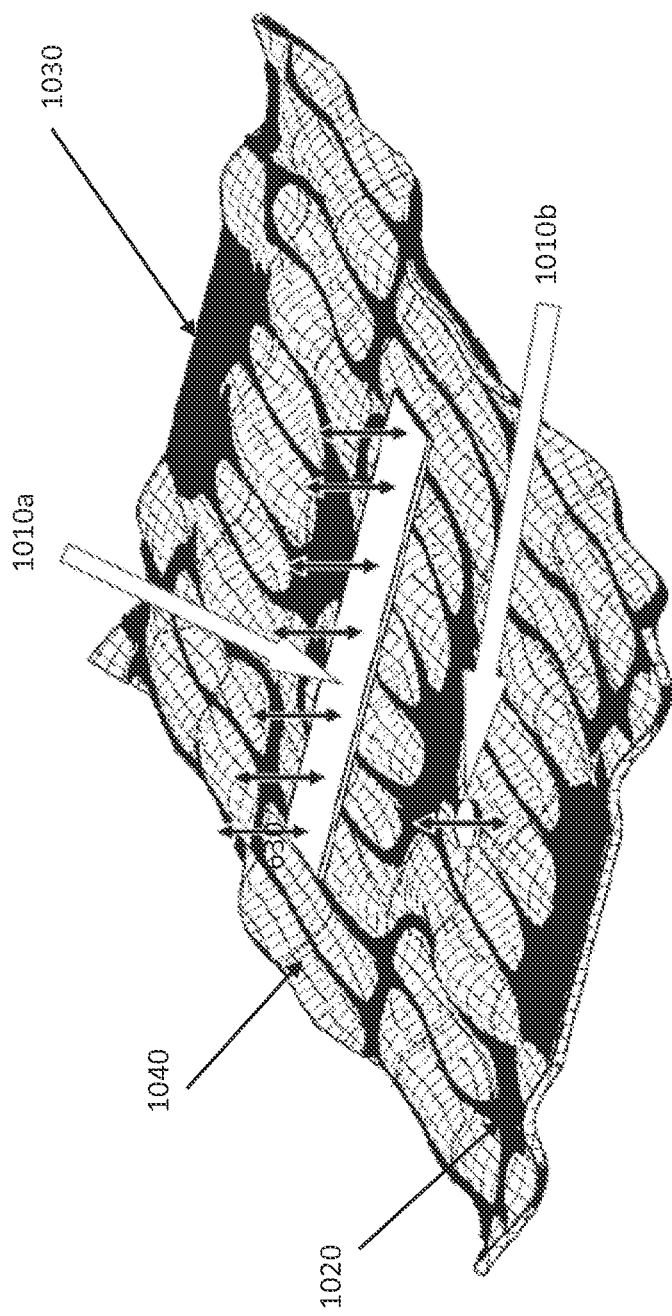
FIG. 6 is a perspective view of an example interaction of contact plates with an excited object.

As shown in greater detail below in FIGS. 10 and 11, acoustic energy sources transfer energy to the object under test via contact plates. FIG. 6 is a perspective view of an example interaction of two contact plates 1010a and 1010b with an excited object. The placement of the contact plates 1010a and 1010b is important to properly excite the object 1030. For illustrative purposes, one contact plate 1010a is placed improperly and a second contact plate 1010b is placed correctly. As in FIG. 5, in FIG. 6, node locations 1020 are represented by solid black areas. Anti-node locations 1040 are represented by peaks in the black and white grid areas of object 1030.

FIG. 6 shows the contact plate 1010*a* placed over multiple neighboring anti-node locations 1040 of the object 1030. With the placement of the contact plate 1010*a* over multiple anti-nodes, portions of the contact plate 1010*a* will come in and out of contact with the object 1030 as the anti-nodes vibrate out of phase. This decoupling can result in energy loss as energy is transferred between the contact plate 1010*a* and the object 1030 and can, in some cases, damage the object 1030, too. As such, the placement of the contact plate 1010*a* is improper. In some implementations, however, practical limitations may require a contact plate to cover multiple anti-nodes, and as such, while less desirable, such placements are not outside the scope of this disclosure.

To limit or eliminate this decoupling effect, a contact plate is preferably placed so that it only interacts with a single anti-node location. As illustrated in FIG. 6, the second contact plate 1010*b* is correctly placed over only one anti-node location 1040. Further, the shape and geometry of the contact plate 1010*b* can be optimized in accordance with the mode shape of the object 1030 to be excited. For example, larger anti-nodes can be excited with larger contact plates, whereas smaller anti-nodes are preferably excited with smaller contact plates. A properly sized and placed contact plate 1010*b* results in maximum energy transferred between the object 1030 and the contact plate 1010*b* and limits decoupling.

In some implementations, if a contact plate is improperly sized, the object 1030 can be damaged as a result of too much heat generation without adequate means of cooling or sinking at the excitation point. To limit or eliminate heat damage to the object 1030 during excitation, several methods of heat rejection can be used. One method for rejecting heat during excitation at the excitation point involves the use of thermal conductivity structures with arrayed fins. The arrayed fins can dissipate heat generated during excitation away from the surface of the object 1030. The fins can be coupled to the surface of the contact plate opposite the object 1030 or elsewhere on the acoustic energy source. Other, active methods for rejecting heat during excitation at the excitation point can involve various circulated fluids, including water, as well as circulated air. Conduits for carrying the cooling fluid can be routed across the surface of the contact plate, for example. In some implementations, the surface of the object 130 may be a material that cannot sufficiently dissipate heat and thus can generate to much heat during excitation, even though the acoustic energy source is sufficiently cooled. In these implementations, the conduits for carrying fluids across the surface of the object 103 can cool the surface of the object 130 during excitation.

Further, in the case of multiple acoustic energy sources; correct placement and phase synchronization of the acoustic energy sources is important to avoid the effects of destructive interference. Preferably, the acoustic energy is applied by the acoustic energy sources in a phase-synchronous fashion. The dynamic force gauge 180 can measure the force being applied at each acoustic energy source to ensure it is applied in a phase-synchronous fashion. For example, if two adjacent anti-nodes are simultaneously driven by separate acoustic energy sources, the excitation driving signals should be 180° out of phase with one another. If "phase synchronicity" is not observed, the excitations will destructively interfere and could cancel the dynamic response of the inspection material. Without the dynamic response, no flaw interactions can be achieved, and no heat generation can be developed. In other implementations, depending on the resonant mode, phase synchronicity may interfere constructively.

Figure 7:
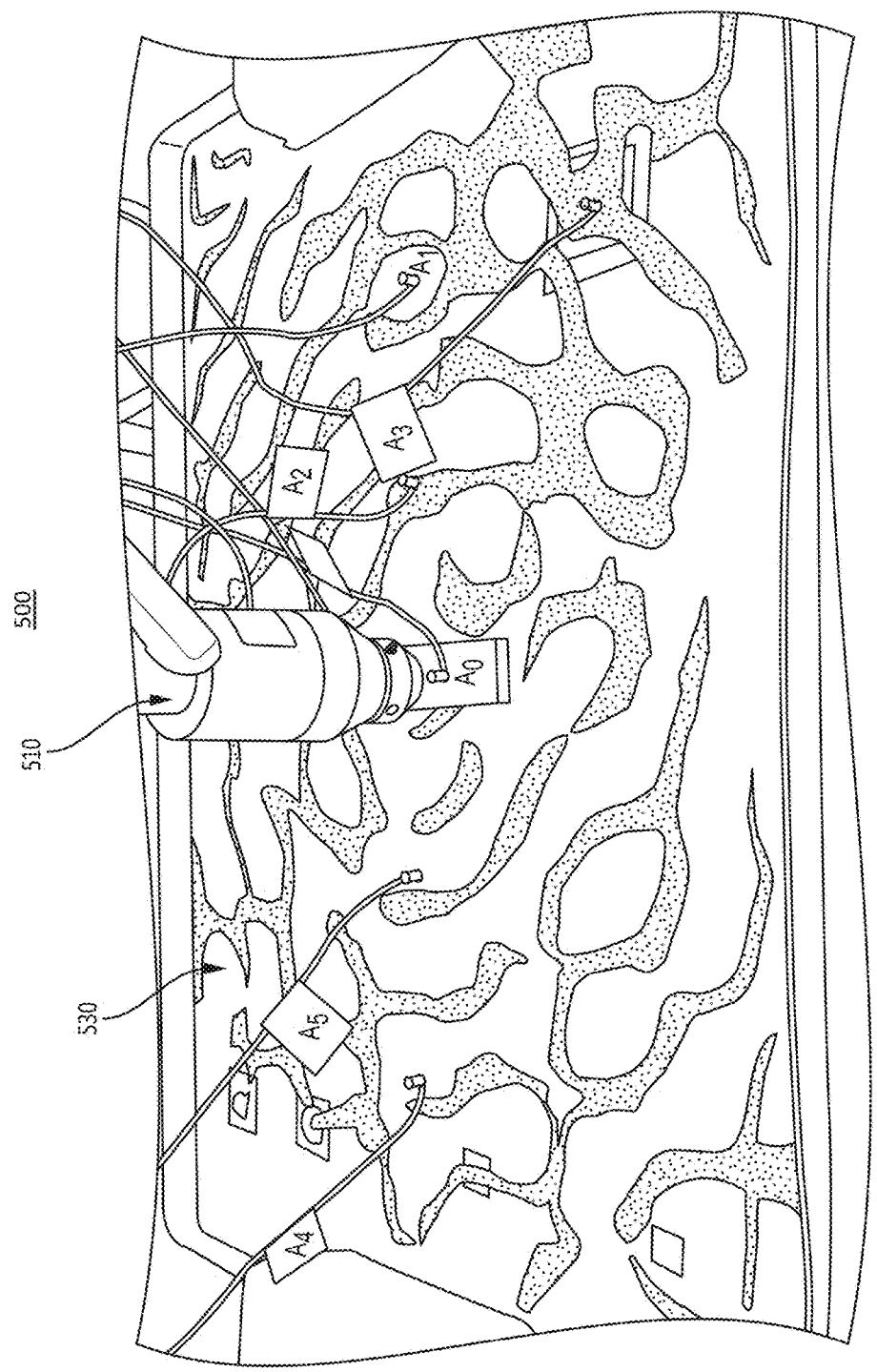
FIG. 7 is an image of an example visual method for identifying object anti-node locations.

Referring back to FIG. 3, in some other implementations of step 302, in which acoustic energy source placement locations are determined, anti-nodes are identified using visual inspection, instead of using a more precise modeling of the modal response of the object. FIG. 7 is an image of an example visual method 500 for identifying object anti-node locations. The method 500 can be used in some implementations instead of the method 400 shown in FIG. 4. As illustrated in FIG. 7, the object 530 is excited by an acoustic energy source 510. Additionally, sand (or some other rather fine granular material) is applied to the surface of the object 530. The acoustic energy source 510 is placed at a 90° angle from the center of the object 530. As acoustic energy is applied to the object 530 from the acoustic energy source, the sand moves to the node locations of the object 530, leaving the anti-node locations bare. The result is the sand collects at node locations, allowing an inspector to visually determine where the anti-node (bare) locations are.

In some other implementations, the modal response of the object 130 can be determined using indirect methods, for example using mathematical modeling techniques to model the object 130. The mathematical methods include Finite Element Analysis. In some implementations, the data for these mathematical formulas can come from previous known data related to the object 130, for example, if detailed engineering design documentation is available with respect to the object under test.

The various anti-node locations identified using any of the above methods can then be selected as acoustic energy source placement locations. The anti-node locations are then excited, in parallel and/or in series (or some in parallel and others in series), at their respective resonant frequencies while being monitored by one or more temperature sensors (e.g., the infrared camera 120 or the embedded temperature sensors 190) as well as motion sensors (such as the Doppler Vibrometer) until a sufficient area of the object 130 has been excited at or in close proximity to a resonant anti-node. A sufficient area may be determined based upon if enough resonant modes are used to excite substantially the entire structure surface such that substantially all of the surface points are at some point during the testing procedure at or in close proximity to an anti-node location. In some implementations, the object 130 may be excited only to a point at which enough heat is generated to be detected by the camera 120 and/or the embedded temperature sensor 190. It should be noted that excitation of a single anti-node location at a corresponding resonant frequency typically results in many more antinodes in nearby portions of the object 130. Thus, not all identified anti-nodes need be selected as acoustic energy source placement locations.

Referring back to FIG. 3, with acoustic energy source placement locations selected, a static preload can be applied to couple the acoustic energy source(s) to the object (Step 304). The static preload force is applied between a contact point, such as a contact plate, of the acoustic energy source 110 and the object 130. In some implementations, the static preload is provided by a vacuum source. The static preload can range from about 100 lbf to about 200 lbf. The static preload mitigates potential damage that can occur during excitation of the object 130 by limiting decoupling between the object 130 and the acoustic energy source 110. The static preload reduces decoupling by holding the acoustic energy source 110 in contact with the object 130 during excitation. Decoupling can cause damage such as impact damage and burning on the object 130. Additionally, decoupling can cause inefficient energy transfer between the acoustic energy source 110 and the object 130. Therefore, the static preload also reduces energy losses as energy is transferred between the acoustic energy source 110 and the object 130. The static preload is applied prior to excitation, but is maintained while the object 130 is excited. In some implementations, the static preload is greater than the acoustic energy applied to the object 130. In one implementation, the static preload is two times greater than a maximum acoustic energy applied to the object 130.

With the static preload applied, the acoustic energy source 110 can excite the object 130 (step 306). The acoustic energy can be applied to the surface of the object 130 in the form of a periodic load from the acoustic energy source 110. The acoustic energy can be applied periodically for a predetermined time. In some implementations, the acoustic energy is applied to the surface of the object 130 for about 90 seconds. In other implementations, the acoustic energy is applied to the surface of the object 130 for a few seconds up to about 10 minutes or any amount there between. Further, the acoustic energy source 110 can apply the acoustic energy at a 90° angle to the sample object 130. In other implementations, the acoustic energy source 110 can apply acoustic energy at various angles dependent upon the shape of the object 130 and/or the shape of the acoustic energy source 110. The acoustic energy source 110 applies acoustic energy at one or more resonant frequencies of the object previously determined to generate maximum displacement in the object at the placement location. With the object 130 excited, a thermal response of the object 130 can be recorded.

As indicated above, while the acoustic energy is applied, the Doppler vibrometer or other motion sensor can monitor the motion of the surface of the object to determine displacement of various regions of the object. This motion monitoring can be used to track the degree with which the entirety of the object has been excited as an anti-node. The object can be continued to be excited at different locations and at different resonant frequencies until a sufficient portion of the object has been excited to a sufficient degree to be confident that all flaws and/or defects have been detected. For example, additional locations can be excited until a completeness confidence factor threshold is reached. The completeness confidence factor provides a metric indicating how confident one can be that sufficient data has been collected that all flaws and/or defects in the object can be found. A process for calculating the completeness confidence factor is described further below.

The method 300 further includes creating and analyzing a thermogram to identify flaws in the object, and if any are found, to characterize the flaws (Step 308). To create the thermogram the camera 120 and/or the embedded temperature sensor 190 can capture the heat generated during excitation. The camera 120 can monitor and detect heat patterns and/or localized heat generation of the object 130. The camera 120 can detect heat generation in two ways, directly and/or indirectly. In the case of direct detection, the camera 120 detects localized heat generation occurring on the surface of the object 130. In the case of indirect detection, when the flaws or defects are internal to the object 130, the camera 120 detects the conduction of thermal energy at the region of the object 130 where the flaws or defects are located. The camera 120 can be communicatively coupled to the processor 160 to transmit data and images.

In some implementations, instead of the camera 120, the embedded temperature sensor 190 can collect metrics related to heat generation on the surface or internal to the object 130. The embedded temperature sensor 190 can be embedded into a specific region of the object 130 and collect temperature changes during excitation. In some implementations, multiple embedded temperature sensors 190 can be embedded into the object 130. Similar to the camera 120, the embedded temperature sensors 190 can detect heat generation in two ways, directly and/or indirectly. In the case of direct detection, the embedded temperature sensor 190 detects localized heat generation occurring on the surface of the object 130. In the case of indirect detection, when the flaws or defects are internal to the object 130, the embedded temperature sensor 190 detects the conduction of thermal energy at the region of the object 130 where the flaws or defects are located. The embedded temperature sensor 190 can be communicatively coupled to the processor 160 to transmit the collected metrics.

FIG. 8 shows a flow chart of an example method of creating and processing a thermogram that can be used by the processor 160 to implement step 306 of the method 300. This step can be carried out by the response analysis module of the processor 160 to determine the thermal response of the object 130 to excitation. For example, the response analysis module can apply a low frequency analysis and a high frequency analysis. The low frequency analysis, as illustrated in FIG. 8, is a process used to determine the presence of a flaw or defect in an infrared image of an object. Together with the high frequency analysis, the two analyses are used to generate estimations for defect size, depth, and location on the object.

First, a thermal difference thermogram is created by comparing an initial image of the object 130, taken prior to excitation, hereinafter referred to as a "cold image", and comparing it to images of the object 130 taken during excitation, hereinafter referred to as "active images" (Step 602). The active images can be combined into composite active images that take into account all of the excitation locations, frequencies and thermal images collected. For example, for each location on the object under test, the temperature in each composite active image can be set to the maximum temperature detected for that location at the corresponding time of excitement. This allows for complete characterization of the defects within the structure even though the defect may not have fully appeared in any one excitation.

The resulting thermograms detail the thermal change in the object 130 from the initial cold image to various active images taken at different times during excitation. This process is advantageous because it eliminates temperature differentials that may have existed in the sample but, were not byproducts of the actual vibrational excitation. Additionally, this process also accounts for emissivity differences from the sample surface and vignette (a byproduct of the optics that causes perception of lower temperatures around the outer edges of the infrared view-field). In some implementations, the low frequency analysis creates the thermal difference thermogram by comparing the metrics collected by the embedded temperature sensor 190, instead of the images from the camera 120.

Next, the thermogram results are filtered to remove noise (Step 604). In some implementations, a linear filter can smooth an image by taking an average value of the pixels in an area of the image and set each pixel to that average value, thereby reducing local variation. Then, the response analysis module can perform a binary conversion to convert the image value to a binary 2-bit image (Step 606). In other implementations, the response analysis module can perform a ternary conversion to convert the image to a ternary 3-bit image.

Next, the response analysis module can apply a density filter to the thermogram (Step 608). The density filter can modify or reduce the intensity of wavelengths or colors in an image. In some implementations, the density filter is applied to improve the appearance of the thermogram. The response analysis module can apply several passes of density averaging to the thermogram. In other implementations, other filtering processes can be used to remove noise from the thermogram without departing form the scope of the disclosure.

Finally, the response analysis module can analyze the thermogram to determine those regions on the object 130 that generated heat (Step 610). If the thermogram indicates a significant temperature change, the high frequency analysis can be applied to analyze the generation at those regions. The high frequency algorithm operates similar to the low frequency algorithm, but the images being compared and analyzed are captured at a higher frequency. Thus, once potential defect locations are detected, the object can once again be excited at locations and frequencies previously determined to excite the potential defect location as an anti-node. Temperature data (e.g., thermal images), however, are captured at a higher frequency (in time) than during the initial tests. Once the high frequency images have been received from the camera 120, the high frequency analysis includes comparing the cold image to the active images (or composite active images as described above) to create corresponding thermograms. Next, the thermograms are filtered to remove noise, converted to a binary or ternary image and filtered using a density filter. As indicated above, in the alternative or in addition, other filtering techniques can be applied without departing from the scope of this disclosure.

The high frequency analysis includes taking each resulting thermogram and determining average temperature values of areas showing increased levels of heat generation. The average temperatures are paired with the time of excitation and this data is used to perform a linear regression. The linear regression shows the temperature change on the surface of the object 130 as the time of excitation increases. The high frequency analysis can then determine and output flaw parameters, for example, the size, thickness, heat generation rate and depth of a flaw or defect of the object 130, by analyzing the final thermogram image and the regression data.

For example, measurements can be taken on areas indicating increased heat generation. The areas indicating heat generation can correlate to a possible flaw. By measuring the geometry of the heat generation areas in the final thermogram, flaw parameters can be determined, including the size, location, and thickness of the flaw. In some implementations, the linear regression graph, which displays the change in temperature of the surface of the object 130 over time, can be used to determine the heat generation rate.

In some implementations, to determine the flaw parameters, the processor 160 compares the generated thermal response data to predicted surface temperature responses for defect of varied size, thickness, heat generation rate, and orientation within an object of varied properties. The following object/environmental properties are used in the equations to complete the transient thermal analysis: thermal conductivity (three-dimensional), convection coefficient, density, and specific heat capacity. These properties are all utilized to produce an equation detailing temperature "T(t, x,y,z,Q,d)" in terms of time of excitation (t), x-location (x), y-location (y), z-location (z), heat generation rate (Q), depth of flaw (d).

Further, the method 300 includes determining a confidence factor (Step 310). In some implementations, the confidence factor calculation module of the processor 160 can be used to determine the confidence factor. In some implementations, the confidence factor is a probability that, after the test procedure, all of the flaws and defects in the object 130 have been found (referred to the completeness confidence factor). In other implementations, the confidence factor value is a probability that the flaw detection system 100 correctly identified and/or characterized a defect or flaw in a suspected area of the object 130 (referred to as a local confidence factor).

In some implementations, a characterization confidence factor can be calculated by comparing the heat generation detected for an identified flaw with a predicted heat generation associated the type of flaw detected. The predicted heat generation rate may be based upon the excitation and average friction coefficients for the different types of flaws. That is, the heat generation rate Q is a function of the friction coefficient $\mu_f$, acceleration a, and the vibratory frequency f. With these relationships, the processor 160 is configured to calculate a minimum expected heat generation rate, for a particular type of defect. For example, a single crack can have just one heat generating surface interaction, while larger impact damage can have hundreds of individual cracks that can all interact with each other to generate heat. By comparing the heat generation rate (determined based on the aforementioned regression analysis) at the location of the identified flaw to the predicted heat generation rate for the determined flaw type, a characterization confidence factor can be calculated indicative of the confidence one can have in the characterization of the flaw.

Figure 9:
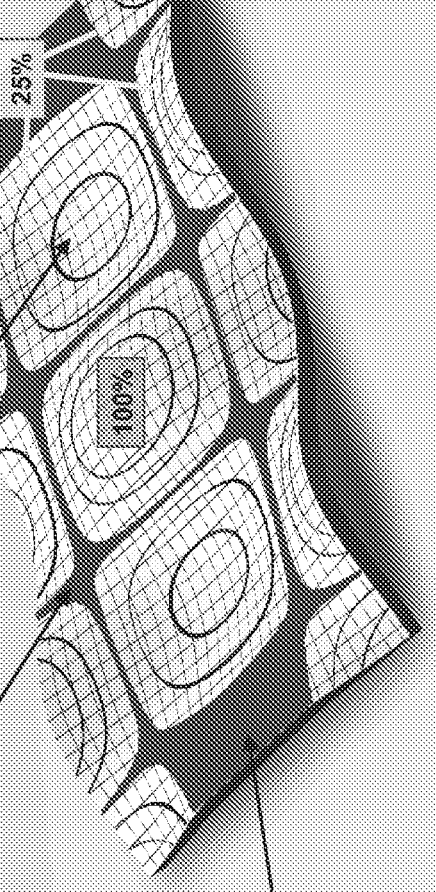
FIG. 9 is a perspective view of a local confidence factor plot.

In some implementations, to determine a local confidence factor for a location on the test object, the processor determines whether the area in question was excited as an anti-node, and if not, how close to anti-node excitation the area experienced. Areas excited as anti-nodes are assigned the highest, and in some implementations a perfect, local confidence factor, whereas locations excited as solely as nodes are assigned a minimum, and in some cases a local confidence factor. Areas which were excited to a degree somewhere between a node and an anti-node are assigned an intermediate local confidence factor corresponding to how close to anti-displacement the area experienced. Example local confidence factors are shown in FIG. 9, which illustrates several nodes 1120 and anti-nodes 1140 on an excited object 1130.

The local confidence factor is indicative of whether the results of the flaw detection and characterization processes described above with respect to the given area are accurate. For example, if an area is found to be absent of flaws or defects in a region with a low local confidence factor, one cannot safely assume that that area is in fact truly without flaws or defects, because the area may just have been insufficiently excited. Similarly, if a flaw were detected, but the location of the flaw was less than fully excited, it is possible that the flaw may be more serious than determined by the flaw characterization process.

To determine the completeness confidence factor, the processor 160 can integrate the local confidence factors across the surface of the object 130. Accordingly, to obtain a perfect completeness confidence factor score, the entirety of the object 130 must be excited as an antinode.

FIG. 10 is a diagrammatic cross-sectional view of an example excitation portion of a flaw detection system 700. FIG. 10 shows certain components of a flaw detection system 700, similar to the flaw detection systems 100 and 200 shown in FIGS. 1 and 2. The flaw detection system 700 includes an acoustic energy source 710, a contact plate 720, and energy transfer material 720. Additionally a static preload 750 is applied between the flaw detection system 700 and the object 730. As illustrated in FIG. 10, the static preload 750 holds the acoustic energy source 710, the contact plate 720, and the energy transfer material 740 in contact with the object 730. The force from the static preload 750 mitigates potential damage that can occur during excitation of the object 730 by limiting decoupling between the object 730, the acoustic energy source 710, the contact plate 720, and the energy transfer material 740.

In the flaw detection system 700, the contact plate 720 is located between the acoustic energy source 710 and the energy transfer material 740. The contact plate 720 transfers the force from the acoustic energy source 710 through the energy transfer material 740 to the object 730. The contact plate 720 also sandwiches the energy transfer material 740 between the acoustic energy source 710 and the object 730. As will be discussed in detail above in regards to FIG. 6, the geometry of the contact plate 720 depends on the size and shape of the acoustic energy source 710 and the geometries of anti-nodes of the object 730 being excited by the acoustic energy source 710.

As illustrated in FIG. 10, the energy transfer material 740 is located between a contact point on the acoustic energy source 710, such as the contact plate 720, and the object 730. The size of the energy transfer material 740 depends on the size and shape of the contact point. The energy transfer material 740 can be a viscoelastic material, an elastic material, or a composite material. For example and without limitations, the energy transfer material 740 can be duct-tape. In some implementations, the energy transfer material 740 includes 3-6 layers of duct tape. In other implementations, the energy transfer material 740 includes a layer of adhesive or glue.

FIG. 11 is a perspective view of another example excitation portion of a flaw detection system 800. More particularly, FIG. 11 shows an acoustic energy source 810, a contact plate 820, and an energy transfer material 840. Similar to flaw detection system 700, a static preload is applied between the flaw detection system 800 and an object 830 under test. In FIG. 11, the static preload 850 is generated by a vacuum source. One or more vacuum cups serve to apply the static preload to the object 830 under test. In some implementations, the vacuum cups can be located on either side of the contact plate 820, as illustrated in FIG. 11. Additionally, in some implementations, the vacuum cups can be an energy transfer material, for example, energy transfer material 840, located between the acoustic energy source 810 and the object 830.

In addition to applying the system and methods described above to detect flaws and defects of certain objects, the systems and methods described herein can test bond joint integrity to determine bond joint strength and stresses. A flaw detection system, such as flaw detection system 100 described in regards to FIG. 1, applies acoustic energy to a bond joint. In some implementations, the acoustic energy is applied to generate a near-uniform shear field across the bond joint.

The application of the acoustic energy to the bond joint creates a dynamic response of the of the bond joint resulting in heat generations at damaged or defective regions of the bond joint. Heat is generated at the failed or failing bond joint due to frictional interactions, such as sliding and clapping, during excitation. The flaws or defects in a bond joint can be in the form of a disband or delamination, which the flaw detection system can find.

While excited by the acoustic energy, the bond joints will be under a stress field including tensile, compressive and shear stresses. Characteristics of the stress field can be determined by modeling the structure and determining the structure mode shapes. Using a motion detection device, the shear field over the bond joint can be analyzed, using methods similar to those described above. The shear field can then be increased by incrementally increasing the acoustic energy source intensity up to a desired shear field test limit, in what is commonly referred to as a mechanical proof test. In some implementations, the mechanical proof test is performed in a static test fashion, in which the bond joint is held in a stationary position. If the bond joint is weak, it will start to fail before the applied stress field exceeds the test limit. The failed bond then acts as a kissing un-bond and under Vibrothermography will generate heat, which will conduct to the surface of the sample will be recorded by devices, such as the camera 120. The processor 160 can then process images of the bond joint under excitation in relation to a pre-excitation thermal image in similar fashion as described above when evaluating surfaces for defects. For example, the processor 160 can generate and analyze thermograms of the bond joint. The thermogram can be analyzed to determine the flaw parameters, including the size, depth, and location of the flaw, as described above. Once the thermogram has been analyzed, a confidence factor may be determined to indicate the completeness that all of the flaws in the bond joint have been found. Additionally, the confidence factor may be used to determine a confidence in the characterization of any identified defects.

In some implementations, when the bond joint begins to fail a shock wave is generated and passed through the bond joint. To detect the shockwave, multiple accelerometers can be added to various locations about the bond joint. Any detected shockwave response can be transmitted to the processor 160. The processor 160 can then analyze the response and to determine the flaw location, size and depth, using methods similar to those described above.

Many variations of the present application will occur to those skilled in the art. Some variations include application with post heating. Other variations call for application using thermal spraying. All such variations are intended to be within the scope and spirit of the present application.

Although some implementations are shown to include certain features or steps, the applicants specifically contemplate that any feature or step disclosed herein can be used together or in combination with any other feature or step on any implementation of the present application. It is also contemplated that any feature or step can be specifically excluded from any implementation of the present application.

While the disclosure has been disclosed in connection with the implementations shown and described in detail, various modifications and improvements thereon will become readily apparent to those skilled in the art. Accordingly, the spirit and scope of the present disclosure is to be limited only by the following claims.

What is claimed is:

1. A method for detecting flaws in an object, the method comprising:

exciting the object at a resonant frequency of the object to determine a plurality of resonant anti-node locations on the object to place a plurality of acoustic energy sources;

applying a static preload between respective contact points of the plurality of acoustic energy sources and the object such that the static preload prevents decoupling between the plurality of acoustic energy sources and the object when the object is excited;

applying acoustic energy to the determined plurality of resonant anti-node locations on the object to excite the object at a respective resonant frequency of the object associated with the respective determined plurality of resonant anti-node locations;

recording a thermal response of the object to the application of acoustic energy;

and analyzing the thermal response to identify flaws within the object.

2. The method of claim 1, wherein determining at least one of the plurality of anti-node locations comprises at least one of analyzing a resonant response of the object or determining a sufficient number of locations such that substantially the entire surface of the object is excited as an anti-node.

3. The method of claim 1, wherein determining at least one of the plurality of anti-node locations comprises visually identifying the at least one anti-node location of the object while exciting the object at a resonant frequency of the object.

4. The method of claim 1, wherein at least one of the plurality of acoustic energy sources is placed in contact with the object via an energy transfer material and a contact plate.

5. The method of claim 1, wherein the static preload is generated by a vacuum source.

6. The method of claim 1, wherein applying the acoustic energy comprises applying the acoustic energy at a frequency ranging from about 100 Hz to about 60 kHz.

7. The method of claim 1, wherein the thermal response is recorded by at least one of: an infrared camera and an embedded temperature sensor.

8. A system for detecting flaws in an object, the system comprising:
a plurality of acoustic energy sources held to the object with a static preload that prevents decoupling between the acoustic energy source and the object when the object is excited, the plurality of acoustic energy sources configured to excite the object at a resonant frequency of the object;
a motion sensor configured to determine a plurality of resonant anti-node locations on the object while the object is excited by one or more of the plurality of acoustic energy sources;
a temperature sensor;
a function generator configured to cause the plurality of acoustic energy sources to apply acoustic energy to the determined plurality of resonant anti-node locations on the object at one or more respective resonant frequencies associated with the respective determined plurality of resonant anti-node locations; and
a processor communicatively coupled to the temperature sensor and the motion sensor, the processor configured to:
receive data indicative of the plurality of resonant anti-node locations on the object from the motion sensor to determine placement locations on the object for the plurality of acoustic energy sources;
receive, from the temperature sensor, data indicative of a thermal response of the object to the application of acoustic energy to the determined plurality of resonant anti-node locations at the one or more respective resonant frequencies; and
analyze the thermal response to identify flaws within the object.

9. The system of claim 8, wherein each of the acoustic energy sources is one of: a piezoelectric transducer, a voice coil, or a rotating eccentric mass.

10. The system of claim 8, wherein the temperature sensor is an infrared camera.

11. The system of claim 8, further comprising an energy transfer material to facilitate transfer of acoustic energy from a contact plate to the surface of the object.

12. The system of claim 8, wherein the motion sensor is at least one of: an accelerometer, a dynamic force gauge, a Doppler vibrometer, and wherein the processor is configured to process the output of the accelerometer, dynamic force gauge, or Doppler vibrometer to determine placement locations on the object for the plurality of acoustic energy sources.

13. The system of claim 12, wherein the processor is configured to generate and analyze thermal difference thermograms based on temperature data received from the temperature sensor before and during excitation of the object by the plurality of acoustic energy sources to determine a transient thermal response of the object.

14. The system of claim 8, wherein the function generator is configured to generate different types of electrical waveforms such that each of the plurality of acoustic energy sources may simultaneously excite the object at different resonant frequencies of the object over the same or different time periods.

15. The system of claim 8, wherein the function generator is a component of the processor.

16. A method for detecting flaws in a bond joint, the method comprising:
exciting the bond joint at a resonant frequency of the bond joint to determine a plurality of resonant anti-node locations on the bond joint to place a plurality of acoustic energy sources;
applying a static preload between a contact point of the plurality of acoustic energy sources and the bond joint such that the static preload prevents decoupling between the plurality of acoustic energy sources and the bond joint;
applying acoustic energy to the determined plurality of resonant anti-node locations on the bond joint to excite the bond joint at respective resonant frequencies associated with the respective determined resonant anti-node locations;
recording a thermal response of the bond joint to the application of acoustic energy; and
analyzing the thermal response to identify flaws within the bond joint.

17. The method of claim 16, wherein the acoustic energy is applied for a time ranging from about 1 second to about 10 minutes.

18. The method of claim 16, wherein analyzing the thermal response comprises comparing an image of the bond joint taken prior to exciting the bond joint to an image of the bond joint taken while the bond joint is being excited to determine a transient response of the object.

19. The method of claim 16, wherein analyzing the thermal response further comprises determining at least one of: a depth of a defect, a size of a defect, or a location of a defect.

20. The method of claim 16, comprising detecting by at least one accelerometer a shockwave resulting from a failure of the bond joint in response to the applied acoustic energy.

* * * * *